United States Patent
Harakawa

(10) Patent No.: US 12,357,972 B2
(45) Date of Patent: Jul. 15, 2025

(54) METAL-SUPPORTING NONWOVEN FABRIC AND PRODUCTION METHOD THEREOF, CATALYST, UNSATURATED COMPOUND HYDROGENATION METHOD, AND CARBON-CARBON BOND FORMING METHOD

(71) Applicant: Ebara Corporation, Tokyo (JP)

(72) Inventor: Hiroaki Harakawa, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 153 days.

(21) Appl. No.: 17/999,683

(22) PCT Filed: May 25, 2021

(86) PCT No.: PCT/JP2021/019742
§ 371 (c)(1),
(2) Date: Nov. 22, 2022

(87) PCT Pub. No.: WO2021/241551
PCT Pub. Date: Dec. 2, 2021

(65) Prior Publication Data
US 2023/0285941 A1  Sep. 14, 2023

(30) Foreign Application Priority Data

May 26, 2020  (JP) .................................. 2020-091324

(51) Int. Cl.
| | | |
|---|---|---|
| B01J 23/44 | (2006.01) | |
| B01J 23/38 | (2006.01) | |
| B01J 31/06 | (2006.01) | |
| B01J 35/23 | (2024.01) | |
| B01J 35/30 | (2024.01) | |
| B01J 35/58 | (2024.01) | |
| B01J 37/02 | (2006.01) | |
| B01J 37/16 | (2006.01) | |
| B01J 37/34 | (2006.01) | |
| C07C 5/03 | (2006.01) | |
| D06M 11/83 | (2006.01) | |
| D06M 14/28 | (2006.01) | |
| D06M 14/32 | (2006.01) | |
| D06M 23/08 | (2006.01) | |
| D06M 101/20 | (2006.01) | |
| D06M 101/32 | (2006.01) | |

(52) U.S. Cl.
CPC ............ *B01J 23/44* (2013.01); *B01J 31/063* (2013.01); *B01J 35/23* (2024.01); *B01J 35/393* (2024.01); *B01J 35/58* (2024.01); *B01J 37/0217* (2013.01); *B01J 37/0228* (2013.01); *B01J 37/16* (2013.01); *B01J 37/344* (2013.01); *C07C 5/03* (2013.01); *D06M 11/83* (2013.01); *D06M 14/28* (2013.01); *D06M 14/32* (2013.01); *D06M 23/08* (2013.01); *C07C 2523/44* (2013.01); *D06M 2101/20* (2013.01); *D06M 2101/32* (2013.01)

(58) Field of Classification Search
None
See application file for complete search history.

(56) References Cited

U.S. PATENT DOCUMENTS

| | | |
|---|---|---|
| 5,326,825 A | 7/1994 | Näsman et al. |
| 9,259,728 B2 | 2/2016 | Kim et al. |
| 10,183,246 B2 | 1/2019 | Castellino et al. |
| 2005/0124765 A1 | 6/2005 | Seko et al. |

FOREIGN PATENT DOCUMENTS

| | | | |
|---|---|---|---|
| CN | 1636575 A | | 7/2005 |
| CN | 101985075 A | | 3/2011 |
| CN | 108978210 A | * | 12/2018 |
| CN | 110670050 A | | 1/2020 |
| JP | 2004-504941 A | | 2/2004 |
| JP | 2005-154973 A | | 6/2005 |
| JP | 2008-221089 A | | 9/2008 |
| JP | 2009-167572 A | | 7/2009 |
| JP | 5417302 B2 | | 2/2014 |
| JP | 2014-071004 A | | 4/2014 |
| JP | 5566368 B2 | | 8/2014 |
| JP | 2015-195827 A | | 11/2015 |
| JP | 5999747 B2 | | 9/2016 |
| JP | 2016-215200 A | | 12/2016 |

(Continued)

OTHER PUBLICATIONS

Japan Patent Office, International Search Report in International Patent Application No. PCT/JP2021/019742, 3 pp. (Aug. 3, 2021).

(Continued)

*Primary Examiner* — Tam M Nguyen
(74) *Attorney, Agent, or Firm* — Leydig, Voit & Mayer, Ltd.

(57) ABSTRACT

A metal-supported nonwoven fabric is provided which enables effective synthesis of a target product when used as a catalyst in a flow reaction. The metal-supported nonwoven fabric comprises a nonwoven fabric containing polyolefin fibers or PET fibers, and metal particles. The nonwoven fabric has grafted side chains bound thereto formed of polyvinylpyrrolidone, polyacrylic acid, or a polymer containing functional groups with unshared electron pairs. The metal particles are supported by the grafted side chains via pyrrolidone groups of the polyvinylpyrrolidone, carboxy groups of the polyacrylic acid, or the functional groups with unshared electron pairs.

3 Claims, No Drawings

(56) References Cited

FOREIGN PATENT DOCUMENTS

| | | | |
|---|---|---|---|
| JP | 2017-070939 A | 4/2017 | |
| JP | 6364125 B2 | 7/2018 | |
| JP | 2019-198603 A | 11/2019 | |
| JP | 2021186705 A * | 12/2021 | ............. B01J 23/44 |
| JP | 2000-258592 A | 9/2022 | |
| KR | 10-2018-0013063 A | 2/2018 | |
| WO | WO 2002/005960 A2 | 4/2014 | |
| WO | WO 2017/002954 A1 | 1/2017 | |

OTHER PUBLICATIONS

European Patent Office, Partial Supplementary European Search Report in European Patent Application No. 21813980.6, 14 pp. (Jul. 8, 2024).

* cited by examiner

METAL-SUPPORTING NONWOVEN FABRIC AND PRODUCTION METHOD THEREOF, CATALYST, UNSATURATED COMPOUND HYDROGENATION METHOD, AND CARBON-CARBON BOND FORMING METHOD

TECHNICAL FIELD

The present invention relates to a metal-supported nonwoven fabric and a method for manufacturing the same, a catalyst, a method for hydrogenating an unsaturated compound, and a method for forming a carbon-nitrogen bond.

BACKGROUND ART

Except in petrochemical processes, a batch reaction is a currently mainstream for synthesizing chemical products. In recent years, however, cost reduction, and safety and productivity improvement have been demanded, and a shift from a batch reaction to a flow reaction is desired in the synthesis of chemical products (especially pharmaceuticals). In the synthesis of chemical products, catalysts are used in various situations. For performing a flow reaction, a supported catalyst, in which a catalytic material is supported by (fixed to) a support, does not require operation for catalyst separation and is thus desirably used.

An example of typical supported catalyst is a particulate catalyst in which a metal as a catalyst is supported on a support, such as active carbon, a silica-based particle, a ceramic-based particle, or a porous material. However, when such a particulate catalyst is packed in a column for performing a flow reaction, the efficiency of contact between a substrate and a catalytic metal is low, and the pressure loss increases, consequently less likely to create efficient flow. Additionally, a particulate catalyst is so dispersive as to be less easy to handle and is structurally less flexible in a reactor.

For catalysts other than a particulate catalyst, for example, PTL 1 discloses a complex containing metal nanoparticles bound to carboxy or carboxylate groups of cellulose nanofibers, obtained by binding cellulose nanofibers and a metal compound and reducing the metal compound. PTL 2 discloses a cellulose catalyst that is metal catalyst nanoparticles supported, by chemical vapor deposition or impregnation, on the surface of a cellulose catalytic support obtained by carbonizing electron beam-treated natural cellulose fibers and substituting oxidizing groups at the surfaces of the fibers using an acid solution. PTL 3 discloses a catalytic fabric filter that is obtained by impregnating a fabric filter base material into an aqueous impregnation liquid containing an aqueous hydrosol of one or two metallic catalyst precursor compounds, dispersed on nanoparticles of an oxide metal support, a dispersant containing one or two primary amines, and a surfactant and thermally activating the metallic catalyst precursor compounds.

However, the catalyst of PTL 1, in which metal nanoparticles are supported at the surfaces of nano-sized fibers, is not easy to handle, and the pressure loss can increase when a large amount of the catalyst is packed into a reaction column. The catalyst of PTL 2, in which the fibers are carbonated, is considered structurally unstable and is not easy to handle, and the structural changes may increase pressure and destabilize the catalytic reaction. Additionally, the manufacturing process is complex and expensive. The catalyst of PTL 3 does not have a ligand to fix the nanoparticle onto the fibers, and thus, the metal nanoparticles can fall off.

PTL 4 discloses a technique to support metal oxide fine particles on a nonwoven fabric. In this technique, ion-exchange functional groups are introduced to the nonwoven fabric by radiation-induced graft polymerization, and the metal oxide fine particles are attached to some of the ion-exchange functional groups. In the radiation-induced graft polymerization, the nonwoven fabric is irradiated with radiation and then immersed in a glycidyl methacrylate solution for a graft polymerization reaction. The resulting grafted nonwoven fabric is immersed in an iminodiethanol aqueous solution or a sulfonating liquid to introduce a iminodiethanol or sulfo group.

CITATION LIST

Patent Literature

PTL 1: Japanese Patent No. 5566368
PTL 2: Japanese Patent No. 5417302
PTL 3: Japanese Patent No. 6364125
PTL 4: Japanese Patent Laid-Open No. 2014-71004

SUMMARY OF INVENTION

Technical Problem

As described above, it is desirable to develop a catalytic metal supported material that enables an efficient synthesis of a target product in a flow reaction and does not require operation for catalyst separation.

An object of the present invention is to provide a metal-supported nonwoven fabric that enables an efficient synthesis of a target product in a flow reaction when used as a catalyst, a method for manufacturing the same, a catalyst including the metal-supported nonwoven fabric, a method for hydrogenating an unsaturated compound using the catalyst, and a method for forming a carbon-nitrogen bond using the catalyst.

Solution to Problem

The metal-supported nonwoven fabric of the present invention comprises: a nonwoven fabric containing polyolefin fibers or PET fibers; and metal particles, the nonwoven fabric having grafted side chains bound thereto formed of polyvinylpyrrolidone, polyacrylic acid, or a polymer containing functional groups with unshared electron pairs, the metal particles being supported by the grafted side chains via pyrrolidone groups of the polyvinylpyrrolidone, carboxy groups of the polyacrylic acid, or the functional groups with unshared electron pairs.

A method for manufacturing a metal-supported nonwoven fabric according to the present embodiments comprises: a step of irradiating a nonwoven fabric containing polyolefin fibers or PET fibers with radiation, and then graft polymerizing N-vinyl-2-pyrrolidone, acrylic acid, or a monomer containing a functional group with an unshared electron pair onto the nonwoven fabric; and a step of immersing the nonwoven fabric, after the graft polymerization, in a solution containing a metal salt or a metal oxide and a solvent.

A catalyst according to the present embodiments comprises the metal-supported nonwoven fabric according to the present embodiments.

A method for hydrogenating an unsaturated compound according to the present embodiments comprises a step of hydrogenating an unsaturated compound in the presence of the catalyst according to the present embodiments.

A method for forming a carbon-nitrogen bond according to the present embodiments comprises a step of performing a reaction for forming a carbon-nitrogen bond in the presence of the catalyst according to the present embodiments.

Advantageous Effects of Invention

The present invention can provide a metal-supported nonwoven fabric that enables an efficient synthesis of a target product in a flow reaction when used as a catalyst, a method for manufacturing the same, a catalyst including the metal-supported nonwoven fabric, a method for hydrogenating an unsaturated compound using the catalyst, and a method for forming a carbon-nitrogen bond using the catalyst.

DESCRIPTION OF EMBODIMENTS

[Metal-Supported Nonwoven Fabric]

The metal-supported nonwoven fabric according to the present invention includes a nonwoven fabric containing polyolefin fibers or PET fibers, and metal particles. The nonwoven fabric has grafted side chains bound thereto, formed of polyvinylpyrrolidone, polyacrylic acid, or a polymer containing functional groups with unshared electron pairs. The metal particles are supported by the grafted side chains via pyrrolidone groups of the polyvinylpyrrolidone, carboxy groups of the polyacrylic acid, or the functional groups with unshared electron pairs. For example, the metal particles form chemical bonds (e.g., coordinate bonds) with nitrogen atoms of the pyrrolidone groups, oxygen atoms of the carboxy groups, or atoms with the unshared electron pairs of the functional groups, and thereby can be supported by the grafted side chains.

In the metal-supported nonwoven fabric according to the present invention, metal particles with smaller particle sizes may be highly dispersed over and uniformly supported on (fixed to) the nonwoven fabric to enable the grafted side chains bound to the nonwoven fabric, i.e., the polyvinylpyrrolidone, the polyacrylic acid, or the polymer containing functional groups with unshared electron pairs, to support the metal particles via the pyrrolidone groups, the carboxy groups, or the functional groups with unshared electron pairs. Consequently, the use of such a nonwoven fabric as a catalyst in a flow reaction can enhance the efficiency of contact between a reaction substrate and a catalytic metal to enable an efficient synthesis of a target product. Also, since the metal particles are supported on the nonwoven fabric, the operation for catalyst separation is not required in the flow reaction. Additionally, since a nonwoven fabric is used as the support, the catalyst produces lower pressure loss than particulate catalysts in the flow reaction and is excellent in handleability. The present invention will now be described in detail.

(Nonwoven Fabric)

The nonwoven fabric, which is a support, contains polyolefin fibers or PET (polyethylene terephthalate) fibers. The polyolefin or PET, used as the fiber material of the nonwoven fabric, easily produces radicals when the nonwoven fabric is irradiated with radiation in graft polymerization described later. Examples of the polyolefin include polyethylene, polypropylene, and an ethylene-chlorotrifluoroethylene copolymer (ECTFE).

The weight per unit area of the nonwoven fabric is preferably 50 g/m2 to 80 g/m2 and more preferably 55 g/m2 to 70 g/m2. When the weight per unit area is 50 g/m2 or more, the durability in terms of using as a catalyst is increased. Also, when the weight per unit area is 80 g/m2 or less, the pressure loss in a flow reaction can be reduced.

(Metal Particle)

The metal of the metal particles can be, but is not particularly limited to, a metal acting as a catalyst. The metal may be, for example, a transition metal, such as a noble metal. Specific examples of the metal include Pd, Pt, Au, Ag, Rh, Ru, Ir, Os, Cu, Ni, and an alloy containing at least one of those metals.

The average particle size ($D_{50}$) of the metal particles is preferably 100 nm or less from the viewpoint of increasing the efficiency of contact between the reaction substrate and the catalytic metal to improve the catalytic activity when used as a catalyst. More preferably, the average particle size ($D_{50}$) is 2 nm to 50 nm, still more preferably, 2 nm to 20 nm. The average particle size ($D_{50}$) is a value measured under a transmission electron microscope (TEM).

(Grafted Side Chain)

The nonwoven fabric has grafted side chains bound thereto, formed of polyvinylpyrrolidone, polyacrylic acid, or a polymer containing functional groups with unshared electron pairs. The term "grafted side chain" used herein is a side chain formed by graft polymerizing a monomer (N-vinyl-2-pyrrolidone, acrylic acid, or a monomer containing a functional group with an unshared electron pair) on the fiber surfaces of a nonwoven fabric. The metal particles are supported by the grafted side chains via the pyrrolidone groups, carboxy groups, or functional groups with unshared electron pairs of the grafted side chains. For example, the metal particles form chemical bonds with nitrogen atoms of the pyrrolidone groups, oxygen atoms of the carboxy groups, or atoms with the unshared electron pairs of the functional groups, and thereby can be supported by the grafted side chains. Examples of the chemical bond include a coordinate bond, an ionic bond, and a hydrogen bond. Whether the metal particles are supported by the grafted side chains via pyrrolidone groups of the polyvinylpyrrolidone, carboxy groups of the polyacrylic acid, or the functional groups with unshared electron pairs can be determined by observation under a transmission electron microscope (TEM).

From the viewpoint that each of the metal particles can be supported at many points by the grafted side chains, polyvinylpyrrolidone, polyacrylic acid, or a polymer containing functional groups with unshared electron pairs is used as the polymer forming the grafted side chains. In particular, polyvinylpyrrolidone is preferred because a plurality of pyrrolidone groups can support and fix each of the metal particles at many points to sufficiently reduce the falling of the metal particles, although the coordination of polyvinylpyrrolidone to the metal of metal particles is weak.

The functional group with an unshared electron pair is a functional group in which at least one atom of the constituent atoms has an unshared electron pair, and examples thereof include an amino group, a carboxy group, and a hydroxy group. Specific examples of the polymer containing functional groups with unshared electron pairs include styrene-based polymers containing any of the primary to tertiary amino groups and poly(methyl methacrylate).

The grafted side chains are formed by graft polymerizing a monomer to the nonwoven fabric. In this operation, a radiation-induced graft polymerization method may be suitably used. The radiation-induced graft polymerization method is a method that can introduce desired grafted side chains onto the polymer backbone of an organic polymer base material (nonwoven fabric) by irradiating the base material with radiation to produce radicals and allowing a monomer to react with the radicals. This method allows free control of the number and length of the grafted side chains and introduction of the grafted side chains into existing polymer materials with various shapes.

The radiation that can be used in the radiation-induced graft polymerization method includes γ rays, electron beams, and ultraviolet rays. Among these, γ rays or electron beams are suitably used in the present invention. The radiation-induced graft polymerization method includes a pre-irradiation graft polymerization method, in which a nonwoven fabric is previously irradiated with radiation and then brought into contact with a monomer for reaction, and a simultaneous irradiation graft polymerization method, in which a nonwoven fabric is irradiated together with a monomer with radiation at the same time. Other methods may be applied, including a liquid-phase graft polymerization method, in which a nonwoven fabric kept immersed in a monomer solution is subjected to polymerization, a gas-phase graft polymerization method, in which polymerization is performed by contacting a nonwoven fabric with the vapor of a monomer, and an impregnation gas-phase graft polymerization method, in which a nonwoven fabric is immersed in a monomer solution and is then removed from the monomer solution for a reaction in a gas phase. In the present invention, any of the methods may be used.

In the present invention, the impregnation gas-phase graft polymerization method is suitable because the nonwoven fabric used as the base material easily retains the monomer solution. The nonwoven fabric, whose mechanical strength does not decrease even when grafted side chains are introduced by radiation-induced graft polymerization method, allows a large amount of grafted side chains to be introduced thereto.

Preferably, the amount of the grafted side chains bound to the nonwoven fabric is 10 to 200 parts by mass relative to 100 parts by mass of the nonwoven fabric. When the amount of such grafted side chains is 10 parts by mass or more, the grafted side chains can sufficiently support the metal particles. Also, when the amount of grafted side chains is 200 parts by mass or less, deformation of the nonwoven fabric and cracks in the fibers are reduced. Thus, the nonwoven fabric can be kept easy to handle. Furthermore, the catalytic metal particles can be prevented from falling off, which occurs when fibers themselves become brittle. The amount of grafted side chains is a value determined by measuring the mass of the nonwoven fabric before the graft polymerization reaction and the mass of the nonwoven fabric after the graft polymerization reaction.

[Method for Manufacturing Metal-Supported Nonwoven Fabric]

The method for manufacturing a metal-supported nonwoven fabric according to the present invention includes the following steps: a step of irradiating a nonwoven fabric containing polyolefin fibers or PET fibers with radiation, and then graft polymerizing N-vinyl-2-pyrrolidone, acrylic acid, or a monomer containing a functional group with an unshared electron pair onto the nonwoven fabric (hereinafter also referred to as a graft polymerization step); and a step of immersing the nonwoven fabric, after the graft polymerization, in a solution containing a metal salt or a metal oxide and a solvent (hereinafter also referred to as a solution immersion step). The manufacturing method according to the present invention may further include a step of adding a reducing agent to the solution immersing the nonwoven fabric (hereinafter also referred to as a reducing agent addition step). The manufacturing method according to the present invention enables the metal-supported nonwoven fabric of the present invention to be appropriately manufactured. Each step will now be described, but the steps of the manufacturing method according to the present invention are not limited to the following steps.

(Graft Polymerization Step)

In this step, a nonwoven fabric containing polyolefin fibers or PET fibers is irradiated with radiation to produce radicals in the polyolefin or PET, and the radicals are allowed to react with N-vinyl-2-pyrrolidone, acrylic acid, or a monomer containing a functional group with an unshared electron pair to graft polymerize the N-vinyl-2-pyrrolidone, the acrylic acid, or the monomer. Preferably, fibers of the nonwoven fabric are formed of polyolefin from the viewpoint that polyolefin easily produces radicals by radiation irradiation. The graft polymerization may be performed by the above-described radiation-induced graft polymerization method.

(Solution Immersion Step)

In this step, the nonwoven fabric after the graft polymerization step is immersed in a solution containing a metal salt or a metal oxide and a solvent. Examples of the metal salt and metal oxide include salts containing the metal of the metal particles described above as cations and oxides of that metal. Specific examples of the metal include Pd, Pt, Au, Ag, Rh, Ru, Ir, Os, Cu, and Ni. The metal salts include chlorides, hydrochlorides, nitrates, and perchlorates. Such metal salt may be used singly or in combinations of two or more. Example of the solvent include water and an alkali solution. The concentration of the metal salt or metal oxide in the solution is preferably 3 mmol/L to 20 mmol/L.

When palladium chloride is used as the metal salt, the solution preferably contains palladium chloride as the metal salt, water as the solvent, and sodium chloride. By adding sodium chloride, the fine particles of the metal can be uniformly formed and supported.

(Reducing Agent Addition Step)

After the solution immersion step, a reducing agent may be further added to the solution immersing the nonwoven fabric to reduce the metal of the metal salt or metal oxide. Examples of the reducing agent include methanol, ethanol, propanol, a polyol, sodium borohydride, and hydrazine. Such reducing agents may be used singly or in combinations of two or more. The solution immersing the nonwoven fabric may be heated to promote the reduction. Whether the metal of the metal salt or metal oxide has been reduced can be confirmed, for example, by XPS (X-ray Photoelectron Spectroscopy) etc.

[Catalyst]

The catalyst according to the present invention includes the above-described metal-supported nonwoven fabric according to the present invention. The type of reaction making use of the catalyst is not particularly limited as long as the metal contained in the metal-supported nonwoven fabric can act as a catalyst in the reaction, and examples thereof include an oxidation reaction, a reduction reaction, and a carbon-nitrogen bond-forming reaction. In particular, the catalyst is preferably used for hydrogenation reaction or carbon-nitrogen bond-forming reaction of unsaturated compounds from the viewpoint that the advantages of the catalyst in a flow reaction can be more effectively used.

[Method for Hydrogenating Unsaturated Compound]

The method for hydrogenating an unsaturated compound according to the present invention includes a step of hydrogenating an unsaturated compound in the presence of the catalyst according to the present invention. The method may be a method of adding hydrogen by organic synthesis and is preferably a flow reaction. For example, a hydrogenating reaction of the unsaturated compound can be continuously performed by packing a reaction tube such as a column with the catalyst according to the present invention and flowing the unsaturated compound and a reducing agent (e.g., hydrogen etc.) through the reaction tube. The method, which uses the catalyst according to the present invention, increases the efficiency of contact between the unsaturated compound and the catalytic metal and, thus, enables an efficient synthesis of the target product. Additionally, the method requires no catalyst separation, and has low pressure loss and excellent handleability. The unsaturated compound may be, for example, an ethylenically unsaturated compound with two or more carbon atoms, and specific examples thereof include ethylene, propylene, butene, hexene, and octene. Other examples include an acetylene-based compound, an aromatic compound, a nitrile group-containing unsaturated compound, and a carbonyl group-containing unsaturated compound.

[Method for Forming Carbon-Nitrogen Bond]

The method for forming a carbon-nitrogen bond according to the present invention includes a step of performing a reaction for forming a carbon-nitrogen bond in the presence of the catalyst according to the present invention. The reaction for forming a carbon-nitrogen bond may be, for example, a reductive amination reaction etc. The method is preferably a flow reaction. For example, an amination reaction for producing a carbon-nitrogen bond can be continuously performed by packing a reaction tube such as a column with the catalyst according to the present invention and flowing an amine compound and a carbonyl compound, and hydrogen through the reaction tube. The method, which uses the catalyst according to the present invention, increases the efficiency of contact between the reactant and the catalytic metal and, thus, enables an efficient synthesis of the target product. Additionally, the method requires no catalyst separation, and has low pressure loss and excellent handleability. In this method, the metal of the metal particles of the catalyst is preferably Pt, Pd, or an alloy thereof.

EXAMPLES

The present invention will be further described with reference to Examples. However, the invention is not limited by the following description.

Example 1

A nonwoven fabric made of polyethylene fibers (product name: OX8901-T6, manufactured by Japan Vilene Company, Ltd., 18 cm×30 cm, weight per unit area: 62 g/m2) was irradiated with an electron beam (245 keV) (applied energy: 150 kGy). The nonwoven fabric was immersed in a diluted solution of 50 mass % N-vinyl-2-pyrrolidone for a reaction at 60° C. for 1 hour to graft polymerize 62 parts by mass of N-vinyl-2-pyrrolidone relative to 100 parts by mass of the nonwoven fabric (grafted side chains: polyvinylpyrrolidone).

Then, 25.7 mg of palladium chloride was dispersed in 50 ml of pure water to prepare a metal salt solution. The nonwoven fabric to which N-vinyl-2-pyrrolidone was grafted was immersed in the metal salt solution. To this solution was added 50 ml of ethanol, and a reduction reaction was conducted in an atmosphere of air for 5 hours with stirring and refluxing at 80° C. Thus, a partially shaded gray metal-supported nonwoven fabric was obtained.

The resulting metal-supported nonwoven fabric was subjected to observation under an SEM (Scanning Electron Microscope) and X-ray analysis, and it was confirmed that metal nanoparticles ($D_{50}$: 100 nm or less) of palladium (Pd) were attached to the metal-supported nonwoven fabric. Also, the binding state was analyzed by XPS, and the peak derived from the metallic bond (0 valences) of palladium was observed at 335.4 eV in a photoelectron spectrum. Also, TEM observation showed a structure with a different contrast around the palladium particles at the surface. This state implies that the palladium particles were fixed, and it was thus confirmed that the palladium particles were supported via the pyrrolidone groups of the polyvinylpyrrolidone forming the grafted side chains.

Example 2

A nonwoven fabric to which N-vinyl-2-pyrrolidone was grafted was produced in the same manner as in Example 1. Then, 344 mg of palladium chloride (about 20 mmol/l of palladium) and 583 mg of sodium chloride (about 5 times equivalent) were added to 100 ml of pure water and mixed to prepare a metal salt solution in which palladium chloride was dissolved as sodium tetrachloropalladate. The nonwoven fabric to which N-vinyl-2-pyrrolidone was grafted was immersed in 50 ml of the metal salt solution, followed by stirring at room temperature for 20 minutes while the metal salt solution was deaerated with nitrogen. Then, 50 ml of ethanol was added to the solution, and a reduction reaction was conducted in a nitrogen atmosphere for 3 hours with stirring and refluxing at 80° C. Thus, an apparently uniform gray metal-supported nonwoven fabric was obtained.

The resulting metal-supported nonwoven fabric was subjected to observation under an SEM and X-ray analysis, and it was confirmed that metal nanoparticles ($D_{50}$: 100 nm or less) of palladium (Pd) were attached to the metal-supported nonwoven fabric. In particular, the palladium X-ray spectrum exhibited the same intensity at three portions on the nonwoven fabric in the field of SEM observation view, suggesting that the uniformity of the palladium particles was further increased compared to Example 1. Also, the binding state was analyzed by XPS, and the peak derived from the metallic bond (0 valences) of palladium was observed at 335.4 eV in a photoelectron spectrum. Also, TEM observation showed that the palladium particles were supported via the pyrrolidone groups of the polyvinylpyrrolidone forming the grafted side chains.

Comparative Example 1

A nonwoven fabric made of the same polyethylene fibers as in Example 1 but not subjected to graft polymerization was immersed in 20 ml of palladium chloride ionic solution. To this solution was added 30 ml of ethanol, followed by deaeration with nitrogen at room temperature. Then, a reduction reaction was conducted with stirring and refluxing at 80° C. Three hours after starting the reduction reaction, most of the black precipitate out of the solution was deposited on the nonwoven fabric, and the reduction reaction was terminated. The precipitate attached on the nonwoven fabric was in such a state as to fall off a part thereof when washed with pure water. The substance attached on the nonwoven fabric was observed under an SEM. This observation showed that deposition of the precipitate was proceeding on part of the fiber surfaces and was, in part, particulate but cracked, thus being in a state likely to fall off the nonwoven fabric.

Also, X-ray and XPS analyses showed that the attached substance was palladium metal (0 valences). However, it was confirmed that the deposition proceeded significantly in some portions and thus nonuniform, and palladium metal particles were in a state likely to fall off the nonwoven fabric. These results suggest that the use of the nonwoven fabric to which grafted side chains formed of polyvinylpyrrolidone, polyacrylic acid, or a polymer containing functional groups with unshared electron pairs are bound enables metal particles to be dispersed uniformly and fixed.

Example 3

A nonwoven fabric containing an amount of grafted side chains bound thereto of 69 parts by mass relative to 100 parts by mass of the nonwoven fabric was produced under the conditions of the grafting reaction in Example 1. The nonwoven fabric was allowed to support palladium particles thereon by the metal fixing method as in Example 2 to yield a metal-supported nonwoven fabric. The produced metal-supported nonwoven fabric was cut into pieces of 16 mm in diameter, and 12 pieces were packed into a SUS reaction tube. Tests of hydrogenation reaction of ethylene were conducted by introducing hydrogen gas in an amount of 3 times to ethylene gas (>99.9%) flowing under two conditions of 2 Nml/min and 4 Nml/min. The reaction tube was placed in a thermostatic bath (water bath), and the reaction temperature was set to 65° C. to 70° C. The reaction pressure was 0.8 MPa. After 1.5 to 2 hours, the reaction gas was collected in a gas bag and analyzed by GC/FID. According to the test results, substantially the entire amount of the ethylene gas was detected as ethane gas under both conditions. These results show that the metal-supported nonwoven fabric according to the present invention enables the hydrogenation reaction of ethylene.

Example 4

The metal-supported nonwoven fabric produced in Example 3 was cut into pieces of 16 mm in diameter, and 21 pieces were packed into a SUS reaction tube. Tests of hydrogenation reaction of 1-octene were conducted by introducing hydrogen gas in an amount of 3 times (14 Nml/min, 28 Nml/min) to 1-octene (>97%) flowing under two conditions of 0.016 ml/min and 0.032 ml/min. The reaction tube was placed in a thermostatic bath (water bath), and the reaction temperature was set to 65° C. to 70° C. The reaction pressure was 0.8 MPa. After 1.5 to 2 hours, the solution sample was collected from a trap that separates gas and liquid and analyzed by GC/FID and GC/MS (qualitative analysis).

According to the test results, 87% of the 1-octene under the condition of 0.016 ml/min was detected as n-octane. Also, 7.5% was detected as 2-octene (the other 5.7% was 1-octene). Under the condition of 0.032 ml/min, 82% of the 1-octene was detected as n-octane. Also, 9.4% was detected as 2-octene (the other 8.6% was 1-octene). These results show that the metal-supported nonwoven fabric according to the present invention also enables the hydrogenation reaction of 1-octene.

The invention claimed is:

1. A metal-supported nonwoven fabric comprising: a nonwoven fabric containing polyolefin fibers or PET fibers; and metal particles, the nonwoven fabric having grafted side chains bound thereto formed of polyvinylpyrrolidone,
    the metal particles being supported by the grafted side chains via pyrrolidone groups of the polyvinylpyrrolidone,
    wherein the metal particles has a metal of Pd, Pt, Au, Ag, Rh, Ru, Ir, Os, Cu, Ni, or an alloy containing at least one of those metals.

2. The metal-supported nonwoven fabric according to claim 1, wherein the metal particles have an average particle size ($D_{50}$) of 100 nm or less.

3. The metal-supported nonwoven fabric according to claim 1, wherein the grafted side chains bound to the nonwoven fabric is in an amount of 10 to 200 parts by mass relative to 100 parts by mass of the nonwoven fabric.

* * * * *